United States Patent
Utz et al.

(10) Patent No.: US 7,260,982 B2
(45) Date of Patent: Aug. 28, 2007

(54) METHOD AND DEVICE FOR DETECTING THE ENTRY OF FUEL INTO THE LUBRICATING OIL OF AN INTERNAL COMBUSTION ENGINE

(75) Inventors: Thomas Utz, Vilshofen (DE); Manfred Weigl, Viehhausen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/182,534

(22) Filed: Jul. 15, 2005

(65) Prior Publication Data

US 2006/0037387 A1    Feb. 23, 2006

(30) Foreign Application Priority Data

Aug. 17, 2004   (DE)   ............. 10 2004 039 836

(51) Int. Cl.
*G01M 15/00* (2006.01)
(52) U.S. Cl. .................... 73/118.1; 73/53.05
(58) Field of Classification Search ............. 73/53.01, 73/53.05, 112, 113, 116, 117.2, 117.3, 118.1
See application file for complete search history.

(56) References Cited

U.S. PATENT DOCUMENTS

| 5,169,785 | A | * | 12/1992 | Altman et al. ............. 436/60 |
|---|---|---|---|---|
| 6,553,812 | B2 | * | 4/2003 | Park et al. ............. 73/54.01 |
| 6,966,304 | B2 | * | 11/2005 | Nagaishi et al. ............. 123/480 |
| 2002/0011095 | A1 | * | 1/2002 | Park et al. ............. 73/54.01 |
| 2003/0196479 | A1 | | 10/2003 | Kasen et al. |
| 2003/0213292 | A1 | * | 11/2003 | Budeiri et al. ............. 73/118.1 |
| 2004/0099252 | A1 | * | 5/2004 | Nagaishi et al. ............. 123/480 |
| 2006/0107734 | A1 | * | 5/2006 | Wang et al. ............. 73/118.1 |

OTHER PUBLICATIONS

Abstract of German Published Non-Prosecuted Patent Application DE 195 18 776 A1 (Hohenner), dated Nov. 28, 1996.
Abstract of German Published Non-Prosecuted Patent Application DE 103 06 857 A1 (Rembold et al.), dated Sep. 2, 2004.
Abstract of German Patent DE 39 04 142 C2 (Gluesing), dated Aug. 23, 1990.

* cited by examiner

*Primary Examiner*—Eric S. McCall
(74) *Attorney, Agent, or Firm*—Laurence A. Greenberg; Werner H. Stemer; Ralph E. Locher

(57) ABSTRACT

A process for enabling the detection of an entry of fuel into the lubricating oil of an internal combustion engine can be implemented relatively simply. The process measures a value representative of the volume of lubricating oil in the internal combustion engine and detects an entry of fuel into the lubricating oil on the basis of an evaluation of results of the measurement which were obtained for different points in time.

13 Claims, 3 Drawing Sheets

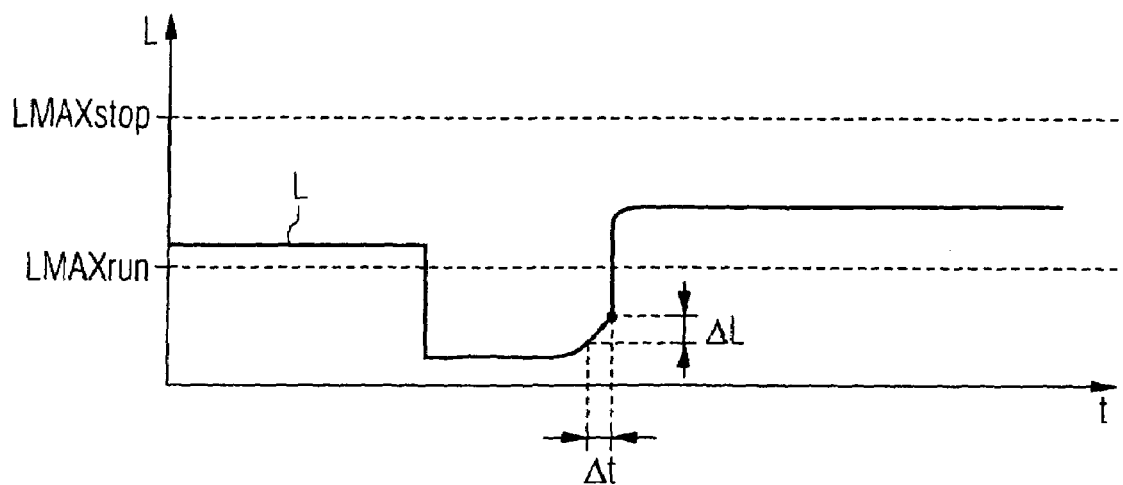
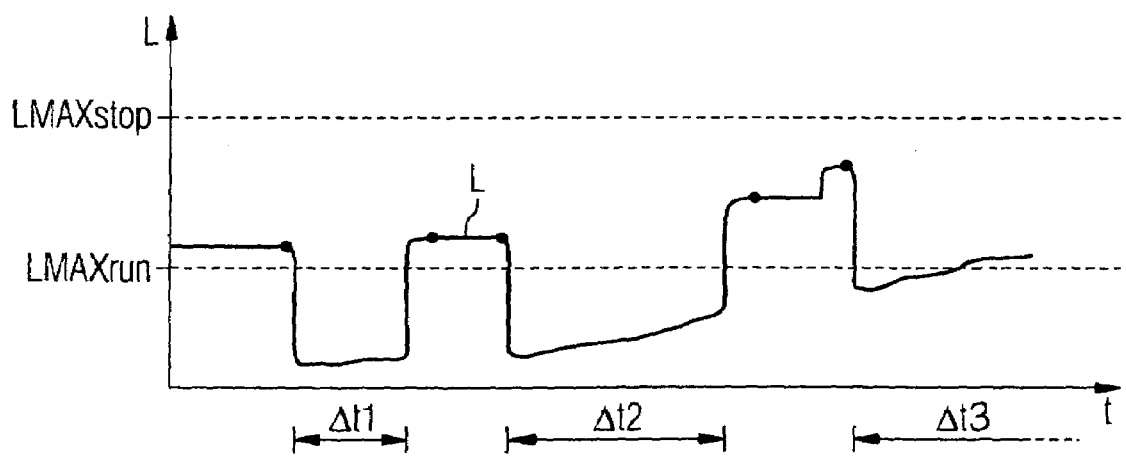

METHOD AND DEVICE FOR DETECTING THE ENTRY OF FUEL INTO THE LUBRICATING OIL OF AN INTERNAL COMBUSTION ENGINE

BACKGROUND OF THE INVENTION

Field of the Invention

The present invention relates to a method as well as to a device for detecting the entry of fuel into the lubricating oil of an internal combustion engine.

The lubricating oil ("engine oil") of an internal combustion engine primarily serves to reduce the friction which causes energy losses and wear between parts of the internal combustion engine moving against each other. In addition the lubricating oil plays a not insignificant role in the cooling of specific engine components, the sealing between engine components which move against one another, the damping of noise as well as with regard to corrosion protection. For these purposes a specific quantity of lubricating oil is kept within the internal combustion engine, with this volume of lubricating oil usually being actively circulated (pressurized recirculating lubrication).

It is well known that the fuel, or non-volatile components of the fuel, can get into the lubricating oil over a period of time with a certain leakage rate.

This entry of fuel into the lubricating oil adversely affects its performance characteristics. In addition with numerous constructions of an internal combustion engine it is possible that the fuel which got into the lubricating oil is eventually added as additional fuel of the combustion.

With the internal combustion engine of a motor vehicle this additional fuel in the combustion mixture, especially when the engine is under part load or idling, can give a higher engine power than is required by the driver. This can lead to a critical or hazardous situation.

SUMMARY OF THE INVENTION

It is accordingly an object of the invention to provide a method and a device for detecting the ingress of fuel into the lubricating oil of an internal combustion engine, which overcomes the above-mentioned disadvantages of the heretofore-known devices and methods of this general type and which provides for an easy-to-implement means of detecting the entry of fuel into the lubricating oil of an internal combustion engine.

With the foregoing and other objects in view there is provided, in accordance with the invention, a method for detecting the entry of fuel into the lubricating oil of an internal combustion engine. The method comprises:

measuring a value representing a volume of lubricating oil present in the internal combustion engine; and detecting an entry of fuel into the lubricating oil based on an evaluation of results of the measurements obtained for different points in time.

In other words, the objects of the invention are achieved with the following steps:

Measurement of a variable representative of the volume of lubricating oil to be found in the internal combustion engine, and Detection of the entry of fuel into the lubricating oil based on an evaluation of the results of the measurement which have been obtained for different points in time.

A basic concept of the invention is to monitor the volume of lubricating oil over time, in order to detect any fuel entering the oil simply and reliably. This especially allows an undesired increase in the power of the internal combustion engine to be prevented well in advance.

Using the basic concept of the invention as a starting point, it is worthwhile in practice taking special measures to guarantee or increase the reliability of the detection, as will be described below.

As regards the reliability of the detection, the problem which arises is that of making the error case in which fuel enters the lubricating oil detectable as "uniquely" and as "early" as possible. The term "unique" here relates both to the reliable detection of an entry of fuel which has actually occurred and also to avoiding an unjustified "error detection", i.e. avoiding an interpretation of the measurement result as an entry of fuel if an entry of fuel is not actually present or has not actually occurred at all It is especially problematic to uniquely assign the cause of a disproportionately large volume of lubricating oil or a disproportionate rise in the volume of lubricating oil to an entry of fuel or to distinguish it from other causes. Such causes, which even without entry of the fuel can lead to an apparent change in the volume of lubricating oil, especially to an apparent increase in volume will be illustrated using an internal combustion engine of a motor vehicle as an example, in which the volume of lubricating oil is measured as the oil level or height in a sump serving as an oil reservoir. The simple evaluation of the oil level in respect of a disproportionate size or a disproportionate increase can for example easily lead to an incorrect diagnosis in the following cases:

Fault in the oil level measurement signal.

Tilting of the sump when driving on an incline.

Centrifugal acceleration operating on the lubricating oil when driving around curves.

In particular the previously mentioned causes of an only apparent change in the volume of lubricating oil can be easily distinguished from a "real" entry of fuel into the oil by essentially taking continuous measurements while the internal combustion engine is running. This should mean that with an increasing duration of uninterrupted running of the internal combustion engine the number and/or the accumulated duration of the measurements increases. For example the measurements can be taken at fixed or predefined variable (e.g. modified on the basis of previous measurements) intervals. The value representing the volume of lubricating oil can be measured continuously in this case at discrete points in time and/or during predetermined measurement intervals. In a preferred embodiment there is provision for measurements to be made at a predetermined time interval (clocked) during the overall running of the internal combustion engine, with this time interval preferably being selected to be smaller than a length of time in which as a result of the construction of the relevant internal combustion engine a perceptible (measurable) increase of the oil volume as a result of the entry of fuel is to be expected.

As a rule such an essentially continuous measurement is not informative or useful while the internal combustion engine is stopped, since in this operating state of the internal combustion engine firstly mostly no entry of fuel is to be expected and secondly this state is also used to top up or change the lubricating oil. It is however of advantage, if while the internal combustion engine is stopped, measurements are taken at least at the beginning and the end of the stopped state. In particular these measurements can be fully evaluated by comparing the measured value of the end of a stopped state immediately prior to an engine run with a measured value at the beginning of a stop state immediately following this engine run, in order to record any change in oil level while the engine has been running and especially an entry of fuel on the basis of an increase in volume.

In a preferred embodiment there is provision for analog measurement of the value representing the volume of oil and conversion of this value into a digital value. This especially enables the storage and evaluation of the measurement to be simplified.

In a preferred embodiment there is provision for a level of a lubricating oil reservoir of the internal combustion engine to be used as a variable representing the volume of the lubricating oil. This is a very simple implementation of the volume measurement which is also provided in any event for many internal combustion engines and in this case can advantageously additionally be used (evaluated) within the framework of the invention.

Preferably the detection of a entry of fuel is signaled visually and/or audibly. This is of great advantage, especially with an internal combustion engine of a motor vehicle, to keep the driver informed. Alternatively or additionally the detected error case can be stored in a diagnostic memory which is usual in motor vehicles. Because of the safety relevance mentioned at the start of an entry of fuel for the internal combustion engine of a motor vehicle is It of great advantage especially with this application if the detection of the entry of fuel is taken into account in controlling the internal combustion engine. For example, on detection of the entry of fuel, the internal combustion engine can be switched off in especially critical cases in a motor vehicle by the engine controller located in a control unit.

The classification as "critical" can be undertaken based on the operating state of the internal combustion engine, especially its temperature. It has actually been shown that an entry of fuel tends to increase the power of the engine at a comparatively higher engine temperature and thus leads to a more dangerous situation than at a comparatively lower engine temperature. With other predefined parameters of the operating state, especially for example at a comparatively low engine temperature, if fuel enters the oil the control unit can also allow what is known as a "limp home" mode, in which the motor vehicle can still be operated but an alarm is signaled to the driver. Preferably this emergency mode includes a forced reduction in engine power. A controlled reduction in engine power, e.g. by corresponding control of a throttle or of the injection system, prevents a critical increase in the engine temperature.

Preferably the measurement and/or the evaluation is undertaken taking into account the operating state of the internal combustion engine. Examples of this are the distinction between engine running and engine stopped already mentioned. In addition further parameters of the operating state can be taken into account, such as the engine revolutions, engine temperature, exhaust parameters etc.

Preferably the evaluation is undertaken with reference to predetermined detection criteria which relate at least in part to the behavior of the measured value over time. An example of this is the criterion already mentioned above of an increase in the volume of the oil which is established by a comparison of the volume of oil immediately before and after the internal combustion engine has run. Alternatively or additionally the timing of the measured values can be checked in a subsection of the engine run to see if such an "increase criterion" is fulfilled. The shorter the time subsection included here, the earlier any entry of fuel can be detected. A time section included for detection of an oil volume increase should however also not be dimensioned too small since otherwise the danger of a misinterpretation because of measuring errors, measuring tolerances and short-term fluctuations increases in significance. With short-term fluctuations of the measured value for the internal combustion engine of a motor vehicle it can for example arise that the apparent oil level in the oil sump varies sharply for a short time when the vehicle is passing over uneven road surfaces.

Especially for suppression of a very rapid change and/or "abnormal" measured values which only last for a very short time, which often because of the vehicle construction cannot relate to an entry of fuel at all, there is provision in a preferred embodiment, within the framework of the measurement and/or the evaluation for the measured value to be averaged over time. For example the measurement signal before the evaluation can be integrated with a time constant which on the one hand is greater than the typically expected duration of non-informative, rapid fluctuations and on the other hand is small enough to guarantee a desired reaction time of detection.

A preferred use of the method in accordance with the invention is obtained for an internal combustion engine with direct fuel injection, with a fuel injector and at least one further component of a fuel injection unit essentially being arranged entirely within a engine block module of the internal combustion engine. This means in particular the case in which there are components of the injection device accommodated within the engine block module which, without restricting their function, could also be accommodated outside the latter. The term "engine block module" here designates the totality of the engine components containing the lubricating oil, that is the "engine block" in the narrower sense and accessories (such as the cylinder head cover etc.), in which the oil is pumped or lubricated or fed (back). With this construction there is an increased danger of an entry of fuel from the injection device area into the lubricating oil. This problem arises especially for common rail diesel engines with injection components within the cylinder head cover, since with leaks in the seals of the components in the high-pressure and/or the feedback area fuel can get into areas of the internal combustion engine in which the lubricating oil is circulating. For example the fuel getting into the crankcase via oil return holes can get from there for example via the crankcase breather, which for reasons of emission reduction comes out into the exhaust tract, as additional fuel into the combustion chamber.

Other features which are considered as characteristic for the invention are set forth in the appended claims.

Although the invention is illustrated and described herein as embodied in a method and device for detecting the entry of fuel into the lubricating oil of an internal combustion engine, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 4 is a diagram of the timing of an averaged oil level, with an entry of fuel being detected at a point of a phase of the engine operation;

FIG. 5 is a diagram of the timing of an averaged oil level, with an entry of fuel being detected at a point of a phase of the engine run.

DESCRIPTION OF THE PREFERRED EMBODIMENTS

Figure 1:
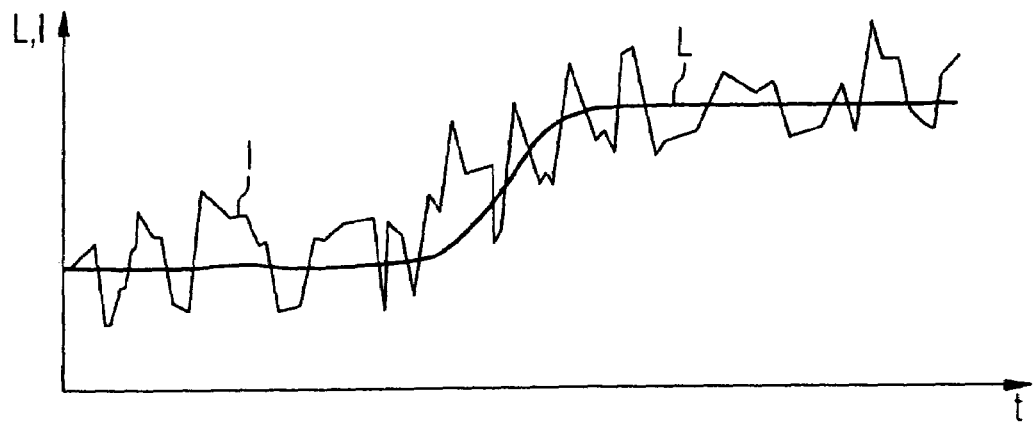
FIG. 1 a diagram of the timing of a measured oil level (l) as well as of an averaged oil level (L) formed therefrom.

Referring now to the drawing figures in detail and first, particularly, to FIG. 1 thereof, there is shown a typical timing graph of a level l of lubricating oil of an internal combustion engine of a motor vehicle while the vehicle is being driven. The symbol t in FIG. 1 designates the time, which typically extends over a period of around one minute here.

The oil level l is a variable representative of a volume of lubricating oil present in the internal combustion engine and is measured in the area of an oil sump in the engine block. The oil level measurement can for example be based on the measurement of an electrical capacitance which exists between electrical conductors, the space between which is filled more or less with the oil, depending on the oil level. The oil level l could for example also be measured by measuring the electrical power consumption of a heating wire, which, depending on the oil level is more or less immersed in the oil and is heated up regulated to a constant temperature or a constant electrical resistance. For the purposes of the invention it is not mandatory for the variable representing the volume of oil to be proportional to the volume of oil. Nor is it mandatory for this variable to be measured with a comparatively high measurement resolution or even stepless. Instead it is also conceivable for this variable to be measured by comparing it with a few threshold values ("threshold value switch"). It is then possible for example to still determine the variable representing the volume of oil sufficiently accurately by evaluation of the timing of threshold values being exceeded/undershot (switching pulses).

In accordance with the invention any entry of fuel into the lubricating oil of the internal combustion engine is detected on the basis of the evaluation of the timing of the measured variable (here: the oil level l). This is possible since the volume of oil increases if such an entry of fuel occurs. However the problem which arises here is that not every increase in the oil volume or the oil level l corresponds to fuel entering the oil.

FIG. 1, by way of example, illustrates comparatively high-frequency changes or fluctuations of the measured oil level l. But these are caused by a movement of the oil in the sump as a result of unevenness in the road surface. Such high-frequency changes of the measured value l which are caused by uneven road surfaces or vehicle vibrations are discriminated by a signal filter with a lowpass characteristic. The result of such a filtering, for example an integration of the measured value l with a specific time constant, is shown by the curve L in FIG. 1. This curve represents the averaged oil level which is employed for the detection of fuel entering the oil as described in greater detail below. In the example shown the time constant of the integration amounts to a number of 10 second periods. This time constant is expediently to be matched to the relevant application.

For the case of the internal combustion engine of a motor vehicle however the averaged oil level L also exhibits changes which are not caused by fuel entering the oil. Instead such a change of the derived value L can be caused by a particular driving state for example, such as negotiating a curve, accelerating or decelerating, or driving up or down an incline. The increase in the averaged oil level L which can be seen in the middle of FIG. 1 could for example be caused by entering a corner where the lubricating oil located in the sump sloshes around in the direction of the level measuring device.

Changes to the oil L which are caused by such particular driving states can however be distinguished relatively reliably on the basis of the change characteristics from those changes which are the result of fuel entering the oil. Preferably fuel entering the oil is thus detected on the basis of an evaluation with reference to predetermined detection criteria which relate to the timing of the oil level L and which take account of the different change characteristics. To increase the reliability a number of such criteria can be combined with each other.

Suitable criteria for the detection of fuel entering the oil are in particular:

a) during the running of the engine the oil level L rises gradually;

b) the difference in the oil level after the engine has run and before the start of this engine run and lies within a specific range.

To check the criterion a) it is advantageous for the oil level to be measured substantially continuously while the internal combustion engine is running.

By contrast, to check the criterion b) it is sufficient for measurements to be taken while the engine is stopped at the beginning and the end of the stopped period.

Both criteria can be included for the detection if the measurement and/or the evaluation is undertaken taking into account the running state of the internal combustion engine. The information about whether or not the internal combustion engine is running is available for example from a controller of internal combustion engine of a motor vehicle with which the operation of the internal combustion engine is controlled. It is thus expedient to implement the evaluation of the measurement results in the controller itself or in a unit which communicates with it. This also has the advantage that further operating parameters representative of the operating state of the internal combustion engine can be taken into account during detection, such as the engine speed, the engine temperature, exhaust parameters, etc.

Figure 2:
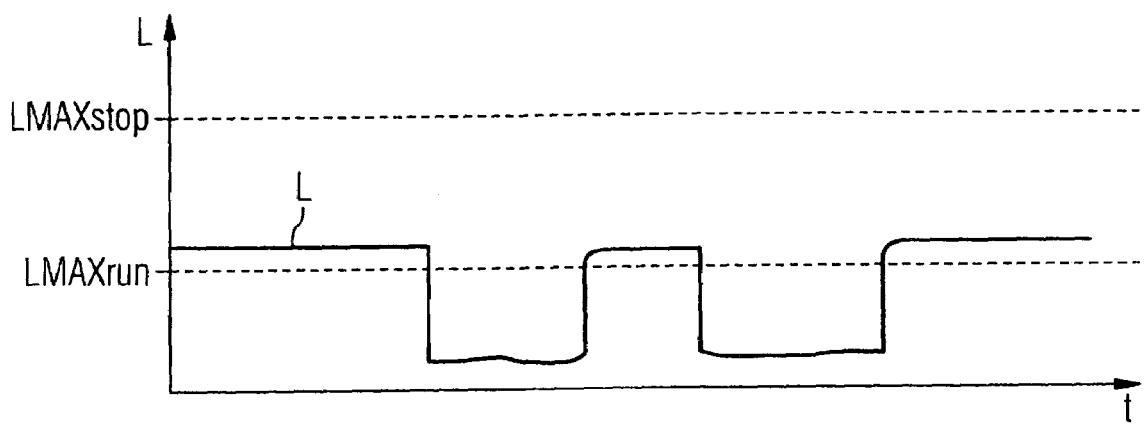
FIG. 2 is a diagram of the timing of an averaged oil level.

FIG. 2 shows a typical timing diagram of the (averaged) oil level L. The diagram shows a period of approximately one hour in which the internal combustion engine is run twice, which can be seen in the figure from the interruptions in the oil level L. When the engine is stopped the entire volume of oil collects in the sump. Until the engine is started the measured oil level L is thus a basically higher than it is when the engine is running. Expediently a permitted maximum value (depending on the engine construction) LMAX-stop is defined, which may not be exceeded at any time.

While the engine is running, a more or less large proportion of the volume of the lubricating oil is circulated in the engine (depending on the engine construction) so that while the engine is running the oil level L is reduced by a proportion which corresponds to the quantity of circulating oil. Expediently a maximum value LMAXrun is also defined for when the engine is running which may not be exceeded while the engine is running.

FIG. 2 illustrates the error-free normal case in which the oil level L always lies beneath the relevant level limits LMAXstop and LMAXrun and on the one hand the oil level L when the engine is stopped and on the other hand the oil level L when the engine is running are essentially the same. Accordingly the result of checking one or both of the criteria a) and b) mentioned above is negative (no fuel entering the oil).

Figure 3:
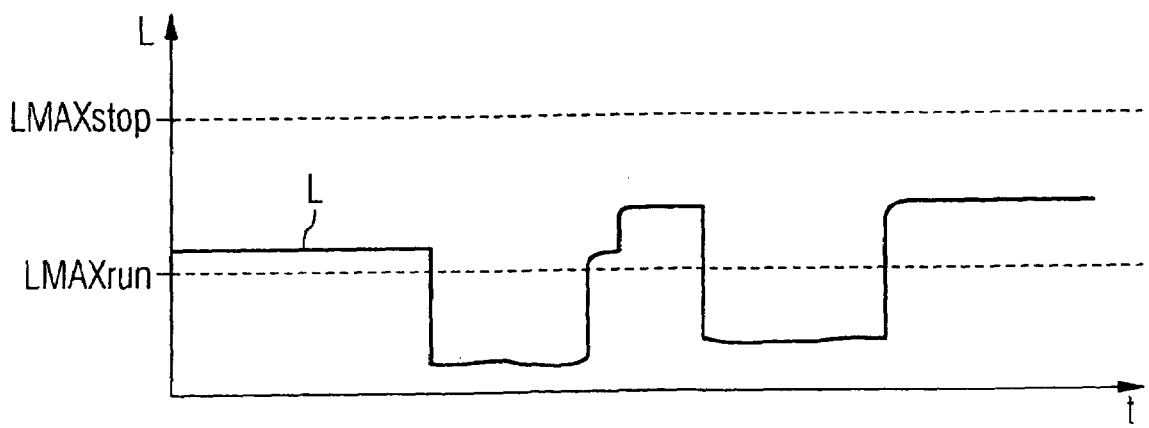
FIG. 3 is a diagram of the timing of an averaged oil level, with oil being topped up at a point of a phase when the engine is stopped.

FIG. 3 is a timing diagram similar to that shown in FIG. 2, but in this diagram, as from a certain point in time (in the phase in the middle of the engine stop period) the quantity of lubricating oil is increased by a certain amount both when the engine is stopped and also when the engine is running. This sudden increase in the oil level L is characteristic of engine oil being topped up, by the user of the motor vehicle for example. In this case too no entry of fuel into the oil is detected on application of the above criteria a) and b) since the oil level L only changes slightly in each case while the engine is running and in particular it does not have any rising tendency viewed over the entire period for which the engine is running and the difference between the oil level L directly before the engine runs and shortly after the same engine run is around zero in each case.

FIG. 4 illustrates the case in which the oil level L rises noticeably while the engine is running, resulting in a forced switch-off of the engine. As an alternative to switching off the engine, on detection of such an increase, putting it the engine into a "limp home" mode also comes into consideration in which operation can be maintained in with mandatory restricted engine power. The detection of the error case is based on a check of the criterion a) mentioned above, which for example can be defined in concrete terms as follows:

a) Fuel has entered the oil at a point in time if in a prespecified period $\Delta t$ immediately preceding this point, the averaged oil level L increases by an amount $\Delta L$ which lies in a range of $\Delta L1$ to $\Delta L2$, with $\Delta t$, $\Delta L1$ and $\Delta L2$ being suitably selected values.

Expediently $\Delta t$, $\Delta L1$ and $\Delta L2$ should be selected so that they depend on the relevant engine construction. In a development current operating parameters can be taken into account for the selection.

If the oil level included for the evaluation is obtained by an averaging over time of a directly measured oil level l with a specific time constant, the above "evaluation period" $\Delta t$ is preferably significantly larger, especially at least 10 times as large as the time constant selected. Especially for detection for the internal combustion engine of a motor vehicle the period $\Delta t$ could be selected for example in the range 10 s to $10^3$ s.

The values $\Delta L1$ and $\Delta L2$ are selected so as to represent the lower limit ($\Delta L1$) or the upper limit ($\Delta L2$) of the expected (or, possibly, typical) entry of fuel for the relevant engine construction within the period $\Delta t$. Since the entry of fuel occurring in the error case may essentially be proportional to the time for almost all engine constructions, it is expedient for a predetermined period $\Delta t$ to select the values $\Delta L1$ and $\Delta L2$ (proportional) to be greater the larger the value prespecified for $\Delta t$.

In a further development of the criterion a) there is provision for the timing of the oil level L to be evaluated simultaneously for a plurality of different periods $\Delta t$ and a corresponding plurality of pairs of values $\Delta L1$, $\Delta L2$ in order to create a certain detection redundancy. There can than be provision for the detection result only to be evaluated as positive if at least one or a predetermined number of such "subcriteria" are fulfilled. Especially with a more complex evaluation of the measured value L it is of advantage for this value to be measured as an analog value and converted into a digital measured value before evaluation. This digitized measured value can then be evaluated with reference to criteria which are implemented by software in a programmable device such as the microcontroller of a engine control unit.

Especially with the internal combustion engine of a motor vehicle it is preferable for safety reasons to take account of the result of the detection in the control of the internal combustion engine, especially to switch off the engine if an error occurs for example or to put it into the emergency operating mode previously mentioned. Which of these two states the internal combustion engine is to be put into if an error occurs can expediently be decided taking into account the result of the detection as well as further operating parameters of the internal combustion engine. An engine switch-off can for example be initiated if while the engine is running the oil level L exceeds the value LMAXrun or the oil, level L with a comparatively hot engine lies slightly below this limit value but exhibits a rising tendency. On the other hand emergency driving mode can be initiated if, while the engine is running the oil level L increases markedly but firstly lies below the limit value LMAXrun by a predetermined amount and secondly the engine temperature lies below a predetermined limit temperature.

FIG. 5 illustrates the oil level L for a period during which the engine runs three times. The phases of the running of the engine are identified by $\Delta t1$, $\Delta t2$ and $\Delta t3$. Each time that the engine runs the oil level L is continuously measured, whereas in the stopped phase measurements are only taken at the positions in the curve highlighted by dots.

During engine running phase $\Delta t1$ fuel begins to enter the lubricating oil, but this occurs at such a low rate that the above criterion a) is not yet fulfilled. The same applies for the above criterion b) since the difference in the oil level L is only slight immediately before and shortly after this engine run. It is illuminating that this difference may in practice be essentially proportional to the duration of the engine run, so that the "difference threshold" used for criterion b) should expediently be selected to be proportional to the duration of the preceding engine run. The difference threshold could also be selected to be proportional to an accumulated (time-integrated) value during the relevant engine run, which "estimates" an instantaneous leakage rate plausible in an error case (e.g. fuel injection rate and/or engine speed etc.).

During the engine run $\Delta t2$ shown in FIG. 5 however a rise in the oil level L occurs which can be recognized both on the basis of criterion a) and also on the basis of criterion b) as characteristic of a faulty entry of fuel into the lubricating oil. With regard to criterion b) it should be pointed out that the measured value L included for generating the difference after the engine run $\Delta t2$ is expediently not recorded immediately after the internal combustion engine is switched off, but after a certain, preferably fixed predetermined wait time (e.g. 10 s). This wait time guarantees that after the internal combustion engine is switched off the proportion of oil previously circulating in the engine has largely returned to the sump. The detection of fuel entering the oil during the timing phase $\Delta t2$ can for example cause the motor controller to place the engine into emergency operating mode.

It can be seen that the oil is topped up in the phase between $\Delta t2$ and $\Delta t3$ while the engine is stopped.

During the third engine run Δt3 the oil level L finally rises above the maximum value LMAXrun predetermined for the engine run. The engine should be compulsorily switched off at this point at the latest.

In a further development of the method for detection of any fuel entering the oil previously described or of suitable criteria for this there is provision for the maximum values LMAXstop and LMAXrun to be predetermined as a function of at least one operating parameter of the internal combustion engine (e.g. speed, engine temperature etc.), especially as a function of the current speed of the internal combustion engine. The latter dependency takes account of the fact that the pump mechanism used to circulate the lubricating oil usually operates as a function of the engine speed so that at higher engine revolutions a lower oil level is to be expected in advance.

Figure 6:
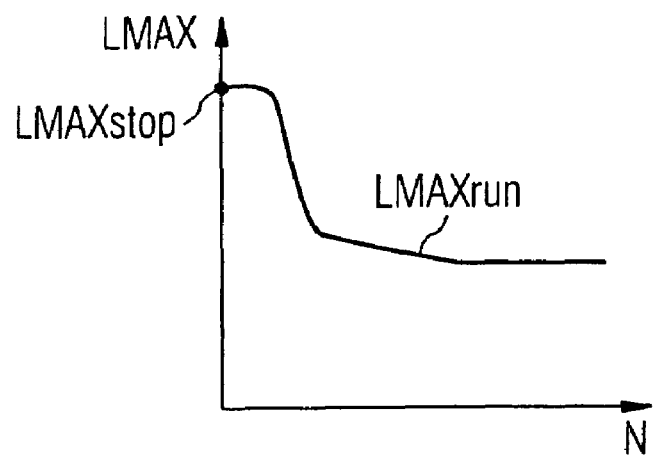
FIG. 6 illustrates how the oil level limit depends on the engine speed and FIG. 7 is a block diagram to illustrate the detection of a fuel entry for an internal combustion engine of a motor vehicle

FIG. 6 shows an example of a speed-dependent maximum value LMAX, which reduces monotonously as the engine revolutions N increase.

Over and above this it is expedient to also take account of engine operating parameters on evaluation of the measurement results. In particular for example the threshold values used for checking the given criteria a) and b) (e.g. ΔL1 etc.) can be selected depending on parameters such as the engine revolutions, the engine temperature, the oil level L etc.

Figure 7:
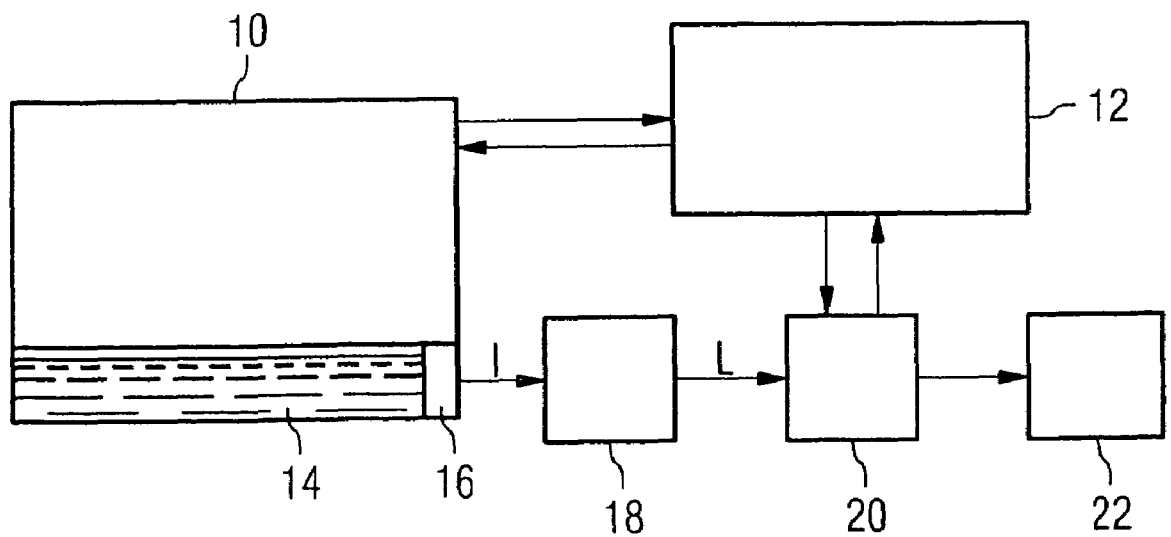

FIG. 7 illustrates schematically a number of components of a motor vehicle equipped with the inventive detection system.

A common-rail diesel engine 10 is controlled by a control unit 12 to which signals such as sensor signals which are representative of the operating state of the engine 10 are entered and which controls devices such as a diesel injection unit (not shown) of the engine 10. Major parts this Injection system (e.g. injector, pump, high-pressure accumulator ("rail"), high-pressure sensor, fuel lines etc.) are attached to the engine in such a way that diesel fuel can get into the oil or into the oil sump 14 of the engine 10 via a possible leak in this area, so that this can lead to oil thinning or oil overfilling In operation of the engine 10 it can arise, as a result of oil overfilling, that the fuel-oil mixture gets into the combustion chamber and leads to an undesired increase in engine revolutions or to an unwanted acceleration of the vehicle. In addition The thinning of the oil can significantly reduce the lubrication capability of the engine oil which can result in damage to the engine.

An oil level measuring device 16 is arranged in the sump 14 which measures the current oil level and enters the measured value into an integration stage 18. In the integration stage 18 the average value over time is formed. Before and after the averaging an analog/digital conversion is undertaken. The averaged measured value L is then fed to an evaluation stage 20 which in the example shown communicates with the engine control device 12 in order on the one hand to obtain operating parameters taken into account for the evaluation from the motor control device 12 and on the other hand to communicate the oil level L as well as the result of the evaluation and/or detection to the motor control device 12. In a variant from the exemplary embodiment shown the evaluation stage 20 can be implemented with the engine control device 12. If an entry of fuel into the lubricating oil of the engine is detected by the evaluation stage 20 during driving this is signaled to the driver of the motor vehicle by means of a signal device 22. In addition an error case of this type is stored in the diagnostic memory of the motor vehicle electronics.

The system shown operates in accordance with a detection method as previously described. Advantageously fuel entering the oil can be detected reliably and that an early stage and distinguished from other effects which can also lead to an (apparent or actual) rise in the volume of oil in the sump. Since a the leakage rates which are possible for the system are known, a meaningful range for all level changes per unit of time while the engine is running can be defined within which the engine will be switched over to operate in emergency mode or switched off as a result of the leakage. Driving around curves or inclines in the road or changes in speed are, when not discriminated by integration stage 18, distinguished by the associated comparatively large temporal change rate of the oil level L from changes resulting from a leakage. The maximum possible fuel leakage rates are limited by system conditions. Therefore a relatively large time window is produced to react to a fuel leakage occurring when the vehicle is being driven which makes for a comparatively reliable method of discriminating between the causes.

With an extremely small leakage rate the detection of the fuel entering the oil is difficult or not possible at all on the basis of the criterion a) mentioned above since firstly the measurement or evaluation is of limited accuracy as a result of the wide variety of influences and secondly for example it is not possible to distinguish between the entry of diesel into the engine oil through a certain unavoidable leakage in the area of the pistons or piston rings. The latter means that the oil level L in the diesel engine 10 can increase under specific preconditions even without the presence of a leak in the injection system. In order to also safeguard against this case or to detect it the above mentioned criterion b) is generally more suitable in this case. If the difference of the oil levels before and after an engine run calculated for this criterion is above a specific amount, a corresponding signal is output. In addition a further engine start can be prevented. To prevent the unnecessary prevention of the engine start if the vehicle is parked on an incline, these types of vehicle driving states or vehicle parking states can be taken into account in the detection. These situations can be detected and taken into account on the basis of the associated specific and characteristic change of the oil level L. To increase the reliability with regard to criterion b) it is especially also possible to only regard entry of fuel into the oil as detected if the criterion b) described above was fulfilled a number of times directly consecutively (after a number of engine runs).

The invention makes it possibly to largely safeguard all conceivable error cases, with preferably suitable criteria being combined with each other and with other engine-specific information which is available in any event.

This application claims the priority, under 35 U.S.C. § 119, of German patent application No. 10 2004 039 836.4, filed Aug. 17, 2004; the entire disclosure of the prior application is herewith incorporated by reference.

We claim:

1. A method for detecting an entry of fuel into lubricating oil of an internal combustion engine, the method comprising:

measuring a value representing a volume of lubricating oil present in the internal combustion engine over time; and detecting an entry of fuel into the lubricating oil based on an evaluation of results of the measurements obtained for different points in time.

2. The method according to claim 1, which comprises taking measurements substantially continuously while the internal combustion engine is running.

3. The method according to claim 1, which comprises taking measurements while the internal combustion engine is stopped, at least following a beginning of a stop period and prior to an end thereof.

4. The method according to claim 1, which comprises measuring the value as an analog value and converting the analog value into a digital measured value.

5. The method according to claim 1, which comprises using a level of the lubricating oil reservoir of the internal combustion engine as the value representing the volume of lubricating oil.

6. The method according to claim 1, which comprises, if an entry of fuel into the oil is detected, signaling the entry visually and/or audibly.

7. The method according to claim 1, which comprises taking the detection into account for a control of the internal combustion engine.

8. The method according to claim 1, which comprises taking account of an operating state of the internal combustion engine in the evaluation.

9. The method according to claim 1, which comprises undertaking the evaluation based on predetermined detection criteria relating to a timing sequence of the measured value.

10. The method according to claim 1, which comprises using the results of the measuring and/or evaluation to form an average of the measured value over time.

11. A device for detecting an entry of fuel into lubricating oil of an internal combustion engine, comprising:

measurement means and evaluation means for executing the method according to claim 1.

12. The method according to claim 1, additionally including:

providing an internal combustion engine with direct fuel injection, wherein parts of an injection device are arranged in the internal combustion engine such that a possible leak at the parts may cause fuel to enter directly into cavities containing lubricating oil of an engine block module; and the detecting step being used to detect an entry of the fuel into the lubricating oil of the internal combustion engine.

13. The method according to claim 1, additionally including:

providing an internal combustion engine with direct fuel injection, wherein a fuel injector and at least one further component of a fuel injection device are disposed substantially completely within an engine block module of the internal combustion engine; and the detecting step being used to detect an entry of fuel into the lubricating oil of the internal combustion engine.

* * * * *